United States Patent
Laycox et al.

(10) Patent No.: US 12,343,280 B2
(45) Date of Patent: Jul. 1, 2025

(54) APPARATUS AND METHOD FOR ICE WATER IMMERSION THERAPY

(71) Applicant: Polar Products Inc., Stow, OH (US)

(72) Inventors: Michael B. Laycox, Dayton, OH (US); William S. Graessle, Stow, OH (US)

(73) Assignee: POLAR PRODUCTS, INC., Stow, OH (US)

( * ) Notice: Subject to any disclaimer, the term of this patent is extended or adjusted under 35 U.S.C. 154(b) by 0 days.

(21) Appl. No.: 18/101,691

(22) Filed: Jan. 26, 2023

(65) Prior Publication Data

US 2023/0165707 A1 Jun. 1, 2023

Related U.S. Application Data

(60) Division of application No. 14/656,056, filed on Mar. 12, 2015, now Pat. No. 11,642,240, which is a continuation-in-part of application No. 13/650,584, filed on Oct. 12, 2012, now abandoned.

(51) Int. Cl.
  *A61F 7/00* (2006.01)
  *A61F 7/10* (2006.01)
  *A61H 35/00* (2006.01)

(52) U.S. Cl.
  CPC .......... *A61F 7/0053* (2013.01); *A61F 7/103* (2013.01); *A61H 35/00* (2013.01); *A61F 2007/0056* (2013.01); *A61H 2035/004* (2013.01); *A61H 2201/0111* (2013.01); *A61H 2201/1604* (2013.01)

(58) Field of Classification Search
  CPC ...... A61F 2007/0002; A61F 2007/0018; A61F 2007/0029; A61F 2007/0039; A61F 2007/0056; A61F 2007/0096; A61F 7/0053; A61F 7/103; A61H 2035/004; A61H 2201/0111; A61H 2201/0214; A61H 2201/1604; A61H 2201/1607; A61H 35/00
  See application file for complete search history.

(56) References Cited

U.S. PATENT DOCUMENTS

| | | | | |
|---|---|---|---|---|
| 5,119,519 A | * | 6/1992 | Foreman | A47G 9/1045 5/640 |
| 2002/0196953 A1 | * | 12/2002 | Burke | H04R 1/1016 455/100 |
| 2005/0096714 A1 | * | 5/2005 | Freedman, Jr. | A61F 7/0053 607/104 |
| 2010/0324635 A1 | * | 12/2010 | Kreck | A61M 16/0479 607/105 |

* cited by examiner

*Primary Examiner* — Tigist S Demie
(74) *Attorney, Agent, or Firm* — Renner, Kenner, Greive, Bobak, Taylor & Weber Co., LPA

(57) ABSTRACT

An emergency management system having an ice water immersion bag capable of rapidly cooling an overheated individual's body through its combination of elements, apertures, and capacity. An overheated individual is placed within the ice immersion bag, yet the individual's body may still be accessed in the event of a medical emergency through the use of one of the many openings presented throughout the bag. The openings otherwise remain sealed and waterproof to prevent the ice water from escaping the bag, further effectuating ice water immersion to rapidly cool the overheated individual.

4 Claims, 7 Drawing Sheets

APPARATUS AND METHOD FOR ICE WATER IMMERSION THERAPY

RELATED APPLICATIONS

The present application is a Division of application Ser. No. 14/656,056, filed on Mar. 12, 2015, now U.S. Pat. No. 11,642,240, which was a Continuation in Part of U.S. Ser. No. 13/650,584 filed on Oct. 12, 2012, now abandoned.

BACKGROUND OF THE INVENTION

1. Field of the Invention

The present invention is directed generally to the emergency management of elevated body temperatures resulting from heat stroke, trauma and post cardiac arrest and, more particularly, to an apparatus and method for the emergency application of ice water immersion therapy.

2. Description of the Related Art

Hyperthermia is an elevated body temperature due to failed thermoregulation. Hyperthermia occurs when the body produces or absorbs more heat than it can dissipate. When the elevated body temperatures are sufficiently high, hyperthermia is a medical emergency and requires immediate treatment to prevent disability or death.

The most common causes for hyperthermia are heat stroke and accidental adverse reaction to drugs. Ice water immersion therapy can be beneficial in the prevention and reduction of hyperthermia. Further, ice water immersion is beneficial in the prevention and reduction of swelling to the spinal cord, triggered by trauma. Post cardiac arrest ice water immersion can be of benefit in helping to reduce complications associated with post cardiac arrest.

Heat stroke is an acute condition of hyperthermia that is caused by prolonged exposure to excessive heat or heat and humidity. The heat-regulating mechanisms of the body eventually become overwhelmed and unable to effectively deal with the heat, causing the body temperature to climb uncontrollably. Hyperthermia differs from fever in the mechanism that causes the elevated body temperatures in that a fever is caused by a change in the body temperature set-point.

Heat stroke in particular is the most prevalent cause of hyperthermia and is due to an environmental exposure to heat, resulting in an abnormally high body temperature. Heat stroke may be non-exertional (classic) or exertional, depending on whether the person has been exercising in the heat. Significant physical exertion on a very hot day can generate heat beyond a healthy body's ability to cool itself, because the heat and humidity of the environment reduce the efficiency of the body's normal cooling mechanisms. This is particularly a problem in dealing with organized sports training. For example, in the United States, college and high school football is a fall seasonal sport in which training begins in during the peak of summer. Conditions such as heat, humidity, exercise, and uniforms and equipment that can lead to an insulating effect can all contribute to a greater incidence of the condition.

Conventionally recognized treatments for hyperthermia depend upon the cause, as the underlying cause must be corrected. Mild hyperthermia caused by exertion on a hot day might be adequately treated through self-care measures, such as drinking water and resting in a cool place. However, when the body temperature is significantly elevated, mechanical methods of cooling are used to remove heat from the body and to restore the body's ability to regulate its own temperatures.

Passive cooling techniques, such as resting in a cool, shady area and removing clothing can be applied immediately. Active cooling methods, such as sponging the head, neck, and trunk with cool water, remove heat from the body and thereby speed the body's return to normal temperatures. Drinking water and turning a fan or dehumidifying air conditioning unit on the affected person may improve the effectiveness of the body's evaporative cooling mechanisms (sweating).

In acute incidents, sitting in a bathtub of tepid or cool water (immersion method) can remove a significant amount of heat in a relatively short period of time. In exertional heat stroke, studies have shown that although there are practical limitations, cool water immersion is the most effective cooling technique and the biggest predictor of outcome is degree and duration of hyperthermia. However, in exertional heat stroke, the condition may be the most severe, with the body temperature reaching upwards of about 40° C. and the affected person being rendered unconscious or showing signs of confusion. In such cases hyperthermia is considered a medical emergency that requires treatment in a proper medical facility where more aggressive cooling measures are available, including intravenous hydration, gastric lavage with iced saline, and even hemodialysis to cool the blood.

Therefore, a need exists in cases of hyperthermia medical emergencies to be able to provide some of the aggressive cooling measures normally available in a hospital or emergency room setting by a first responder, such as by an athletic trainer, an emergency medical technician or a paramedic. Consequently, a portable apparatus and non-hospital based method for the emergency application of ice water immersion therapy is needed.

SUMMARY OF THE INVENTION

It is an object of the present invention to provide an apparatus for the emergency application of ice water immersion therapy.

It is a feature of the present invention to provide an apparatus for facilitating a method for the emergency application of ice water immersion therapy.

The present objectives are accomplished by means of a water proof, enclosed clear plastic body bag for the emergency management of heat stroke, trauma and post cardiac arrest that allows rapid victim placement and immediate immersion into cold water/ice water for management of medical and or trauma and cardiac issues which benefit from cold water/ice water immersion. In order to be functional in the emergency environment the device is compact, easy to use, and adapted in such a manner as to allow for advanced trauma or cardiac intervention, monitoring and treatment. According to a preferred embodiment of the present invention, a sealable chamber is provided that allows for placement of a victim. The victim can then be treated on site by a first responder, and be transported to a hospital or emergency room for subsequent or continued treatment or intervention without the need to remove the apparatus or transfer the victim from one device to another.

It is an object of the present invention to provide a device that may be utilized by any medical personnel who, within their work environment, is responsible for rapid management of heat stroke, trauma or post cardiac arrest as it pertains to standard physician protocols.

It is a further object of the present invention to provide an apparatus capable of being utilized from point of care (where victim collapses) to the emergency department.

It is a further object of the present invention to provide such an apparatus having a sealable chamber capable of eliminating dead space within the chamber in order to reduce the amount of cold water/ice water necessary for immersion.

Further still, it is anticipated that various additional features may be incorporated to further adapt the present apparatus to a method for ice water immersion therapy. Such features may include the incorporation of a removable head elevation pillow with an opening for the occipital area to help maintain an open airway as well as reduce the likelihood of water entering the mouth or nose. Ear plugs may further be provided to reduce the incidence of water entering the auditory canal. Access orifices may be formed at predetermined locations to permit EMS or Emergency Room personnel to have access to a victim's right and left arms for Intravenous (IV) placement, Blood Pressure and pulse oximitry monitoring, or the like. An additional access orifice may further be formed near the area of the groin to allow access for placement of rectal temperature probe and urinary catheter if necessary. Further, a rapid water evacuation port may be placed at the inferior end of the device, which when opened will allow very rapid removal of water if necessary. An additional smaller port may also be placed at the inferior end of the device with tubing connected and with a shut off valve that, when opened, will allow for medical staff to slowly remove water from the device when indicated. Further still, the present invention may be made of clear plastic to enable Athletic Trainers, EMS and ER personnel to visualize the water and ice level in the unit and to visualize the patient for improved monitoring especially when the unit is used secondary to trauma.

BRIEF DESCRIPTION OF THE DRAWINGS

Advantages and features of the present invention are better understood with reference to the following and more detailed description and claims taken in conjunction with accompanying drawings, in which like elements are identified with like symbols, and in which:

DESCRIPTION OF THE PREFERRED EMBODIMENTS

Figure 1:
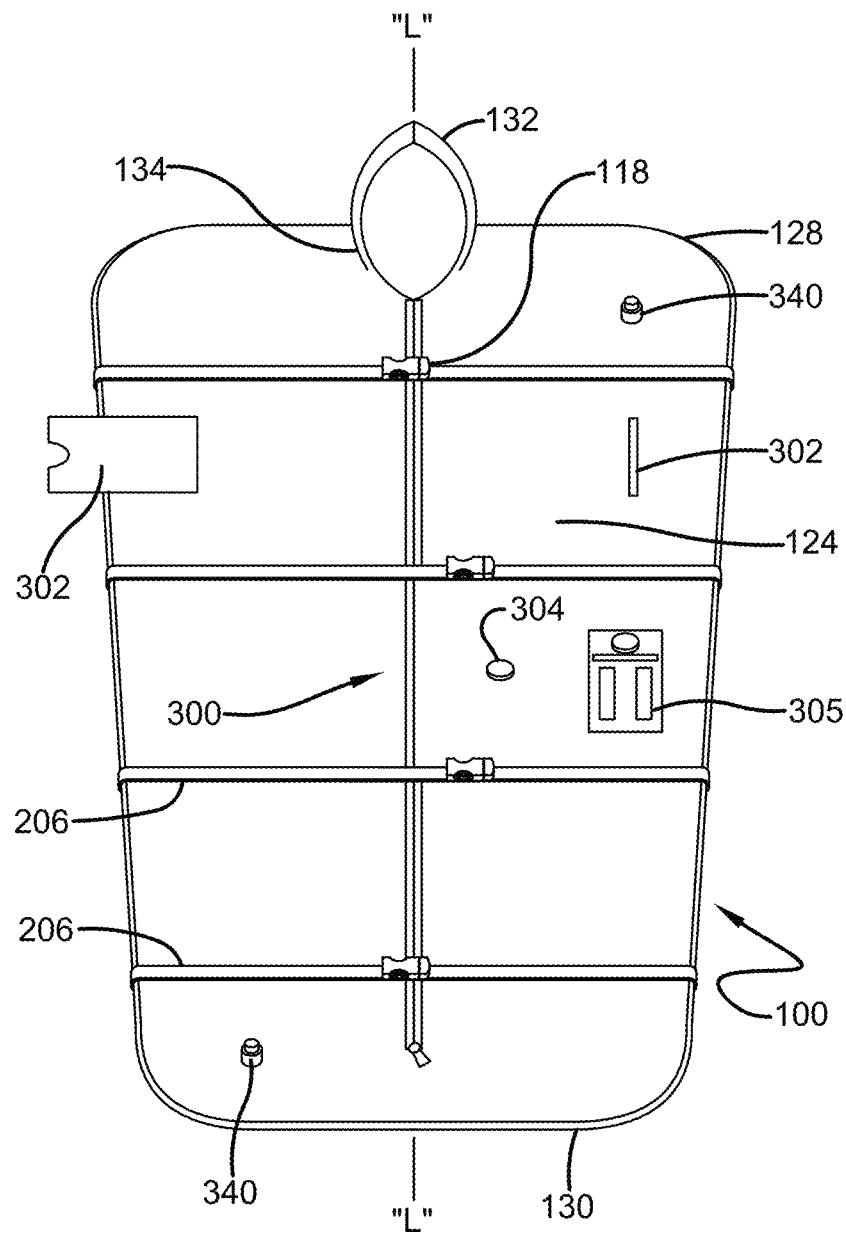
FIG. 1 is a top plan view of an on-demand, reusable ice and water immersion device 100 according to the preferred embodiment of the present 20 invention.
Figure 2:
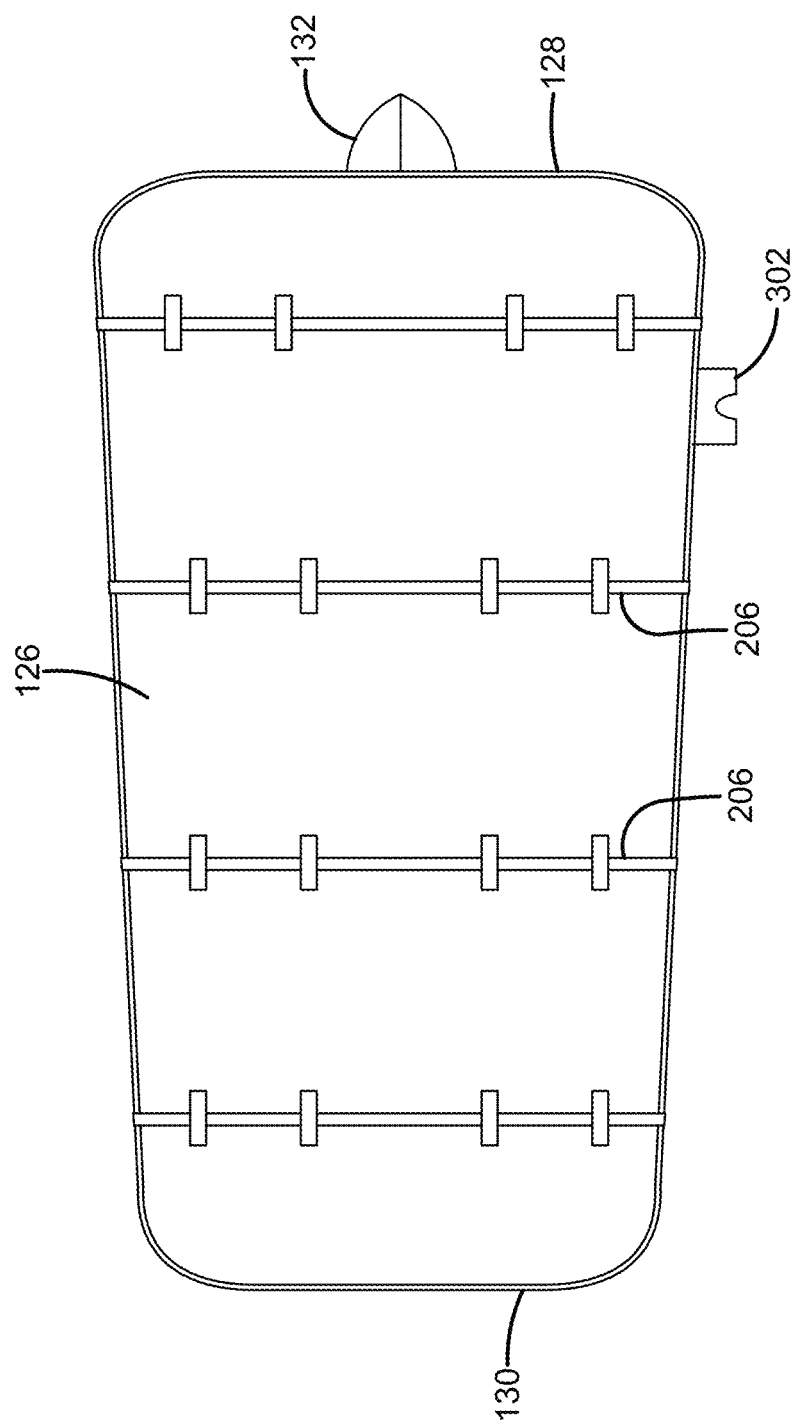
FIG. 2 is a bottom view of the device of FIG. 1.
Figure 3:
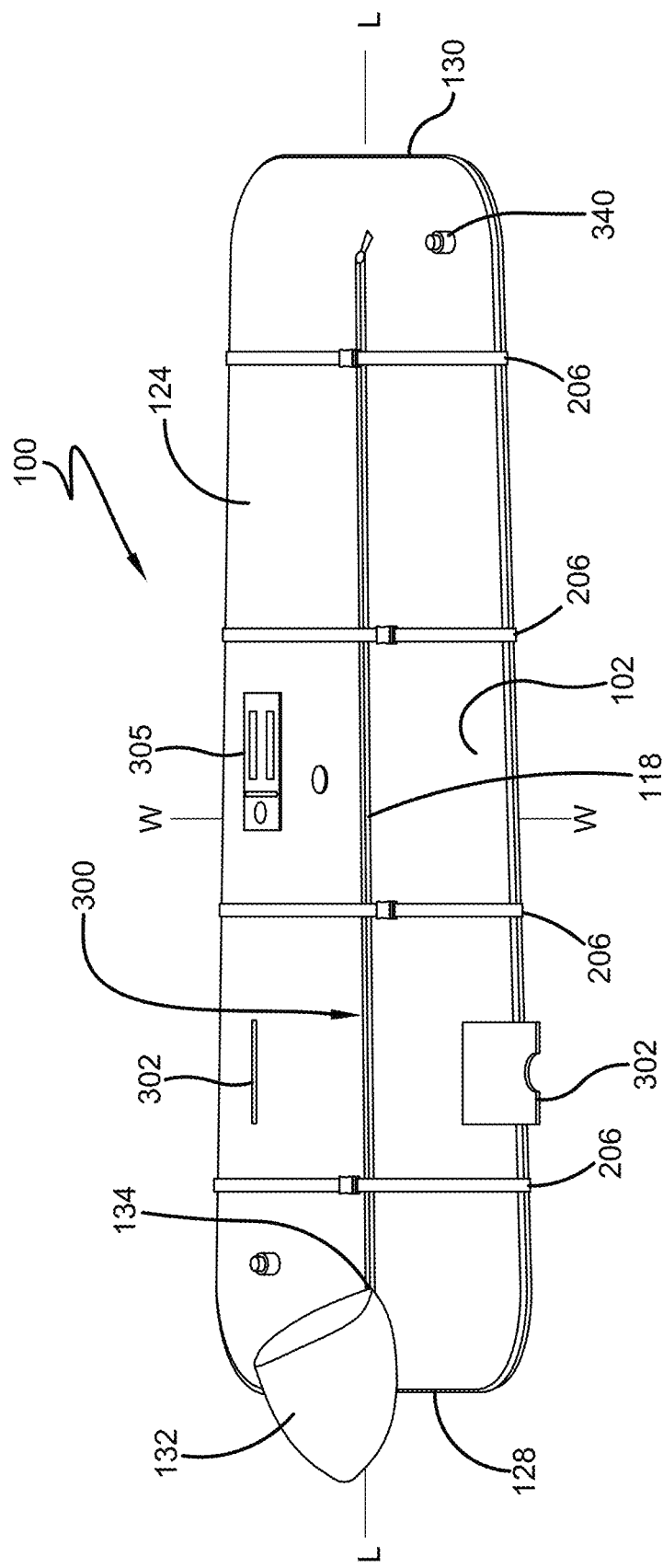
FIG. 3 is a top plan view of a second embodiment of the invention.
Figure 4:
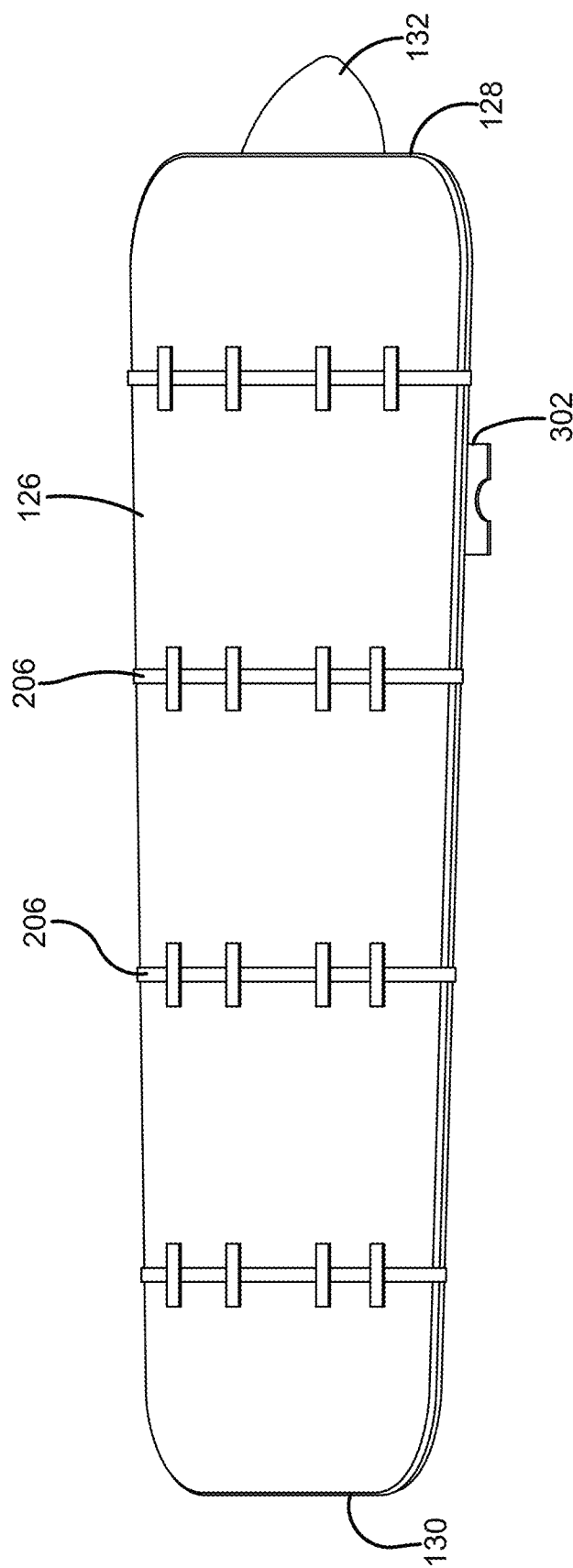
FIG. 4 is a bottom view of the embodiment of FIG. 3.
Figure 5:
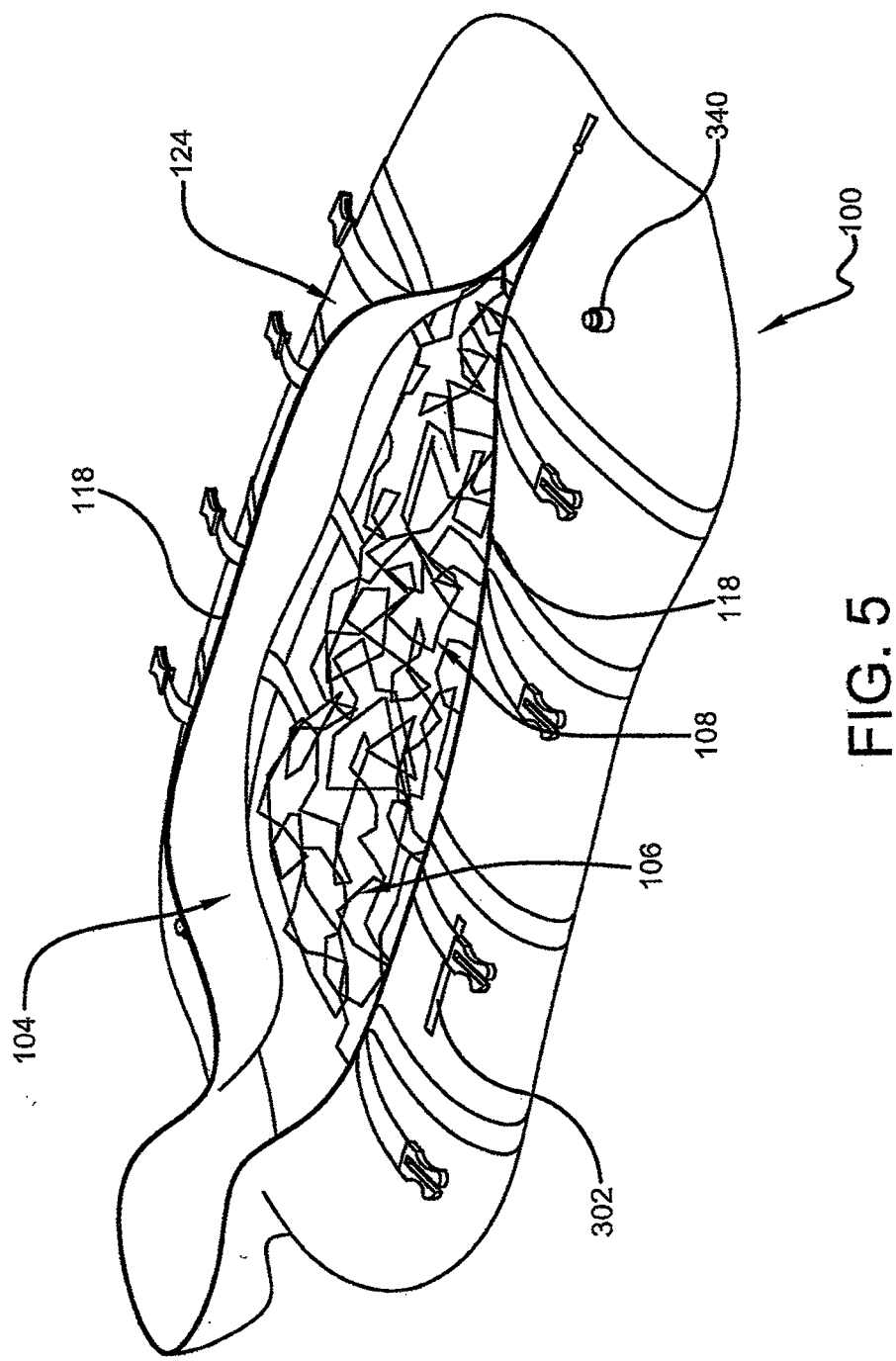
FIG. 5 is a top perspective view of a preferred embodiment of the present invention shown in an open configuration.

In the following description of the invention, reference is made to the accompanying drawings, which form a part thereof, and in which are shown, by way of illustration, an exemplary embodiment illustrating the principles of the present invention and how it may be practiced. It is to be understood that other embodiments may be utilized to practice the present invention and structural and functional changes may be made thereto without departing from the scope of the present invention.

1. Detailed Description of the Preferred Embodiment

As detailed in FIGS. 1-7, an on-demand, reusable ice and water immersion device 100 is shown according to a preferred embodiment of the present invention. The device 100 is formed of a generally pliable bag-like housing that has a closeable contiguous sidewall 102 that forms an internal cavity 104 forming a containment volume capable of receiving and retaining a person and a cooling fluid as will be described in greater detail below. The device 100 may be formed in various sizes, but for purposes of disclosure it is envisioned that a bag 100 having an overall length of approximately 7 feet or 84 inches, would be functionally effective for use with a vast majority of potential patients. It should be understood, however, that such stated sizing should be considered exemplary and that an exact size or dimension should not be viewed as a limitation of the present invention. It should be apparent to one having ordinary skill in the relevant art, in light of the present teachings, that a wide variation in size and dimension should be considered within the range of equivalents of the present disclosure and invention.

The bag 100 is constructed in order to be generally liquid retentive such as to be water proof or water resistant. For purposes of the present invention, the term "water proof or water resistant" is to be defined broadly as generally resisting or slowing the egress of liquid water from the internal cavity 104 when the bag 100 is operationally closed in use. For purposes of the present invention the terms "water proof" or "water resistant" should not be considered narrowly to be restricted only to a leak proof condition or otherwise to mean the complete prevention of liquid from being discharged therefrom, since any minor amounts of leakage or porousness would be considered inconsequential in light of the teachings and functions described herein broadly in light of the additional disclosure and claims herein below. The sidewall 102 may be formed of a flexible, pliable polymer material or canvas material. Further, the sidewall 102 may further be formed of a clear, transparent or translucent material, in whole or in part, in order to provide and permit Paramedics, EMS, or Emergency Room personnel to visualize the overheated individual's body. Such visual observation and monitoring by emergency responders may be beneficial for such first responders in assessing and treating an overheated individual.

The bag 100 has a length or vertical directional axis "L" and a width or horizontal directional axis "W". The length L is greater than the width W, with the length L being at least twice the dimension of the width W. When closed, the bag 100 will form a holding volume or cavity 104 (best shown in conjunction with FIG. 7). The thickness of the bag 100 may vary dependent on a number of variables, including the anticipated size and weight of the overheated individual to be placed within the bag 100, as well as the desired target weight of the stored, unused bag 100, the anticipated functional life, the desired target cost, and other design considerations. The device 100 has a top surface 124 and a bottom surface 126. The bag 100 has a cephalad edge 128 and a caudad edge 130. These two edges, 128 and 130 respectively help identify the orientation of how an overheated individual will be placed within the bag 100. The head of the overheated individual will be oriented towards the cephalad edge 128 and the feet of the overheated individual will be oriented towards the caudad edge 130. The cephalad edge 128 further forms a hood pocket 132 that is formed as integrated with the top surface 124. The hood pocket 132 is intended to accept the face of a user patient placed within the containment volume 104 and may further contain a drawstring closure 134 for providing maximum body coverage, clearance of the user's face and airways, and minimizing of leakage out of the bag 100.

The bag 100 may be made of conventional waterproof or water resistant materials. The bag 100 may also be capable of holding at least 350 lbs, including the occupant, ice 106 and water 108.

The bag 100 has an entry portal 300 that runs linearly along the axis L of the top surface 124. The entry portal 300 will be approximately the same length as the vertical edge of the bag 100 and run from the cephalad edge 128 down to the caudad edge 130. The entry portal 300 may be securely closed and sealed providing a waterproof or leak resistant seal when not opened. Various types of waterproof closure means 118 are anticipated as being able to accomplishing this. Exemplary waterproof closure means 118 may include but are not limited to: waterproof zippers (preferably constructed of non-metal material), waterproof hook and loop closures (i.e., Velcro®), waterproof tongue and groove closures (i.e., ZipDry®). It is preferred that whatever the closure means employed, ice water 106/108 is retained within the internal holding volume 104 where the overheated individual is placed, and that the leakages of liquid water 108 is slowed or minimized such as to contain the liquid as a heat transfer medium when placed within the holding volume 104 or generated from the melting of the ice 106.

Waterproof hook and loop closures or waterproof tongue and groove closures may also be used as a means of closing and sealing the entry portal 300. Such an embodiment would reduce a risk of zipper failure. Further, these closures eliminate metal from the device in the event that an MM is ordered from the hospital while the patient is still submerged within the bag.

An alternate embodiment of the present invention provides for the entry portal 300 to be securely closed with a waterproof zipper, further comprising a hook and loop closure covering the waterproof zipper for added sealing protection.

The hood 132 and entry portal 300 together functions to allow the entire body of the user to be in contact with the icewater 106/108, while allowing the face of the overheated individual to be exposed. This provides clearance of the user's airways, as well as allows for a tracheotomy or other emergency procedure to be performed under emergency circumstances.

The bag 100 has a plurality of cocooning straps 206. While many numeric intervals of cocooning straps 206 are available, the preferred embodiment of the present invention has four parallel spaced cocooning straps 206. Each respective strap 206 is intended to circumscribe about the bag in parallel with the horizontal directional axis of the bag 100. The cocooning straps 206 are spaced evenly apart along the vertical axis relative to each other. The cocooning straps 206 function to securely encapsulate the overheated individual within the bag 100. The cocooning straps 206 effectively cinch down or cocoon the overheated individual.

The cocoon straps 206 are a quick fasten and quick release design. An alternate embodiment of the present invention provides that the device is adjustable to accommodate individuals of all sizes. The cocoon straps 206 are further essential in that they decrease the holding volume 104 inside the bag 100 by effectively cinching down the bag closer to the individual's body. Reducing the holding volume 104 is an important feature because if ice water 106/108 is in limited supply to the first responder, the holding volume 104 will be smaller and allow the ice water 106/108 to fully encapsulate the overheated individual's body within the bag 100.

While the bag 100 of the design shown is capable of being lifted, moved and manipulated without the necessity of carrying straps, in an alternate embodiment a plurality of carrying straps may be provided as permanently attached and secured evenly spaced along each vertical edge of the bag 100.

The bag 100 may be further provided forming a plurality of openings strategically placed about the top surface 124. Alternate configurations may be provided in various embodiments to allow for different numbers and arrangements of openings herein described. In the preferred embodiment of the present invention, at least one, and preferably a pair of intravenous (IV) openings 302 is provided to allow for access to the user's arms, or egress of either of the user's arm from within the containment volume 104 while minimizing any loss of heat transfer. The IV openings 302 are located on the top surface 124 proximate to the vertical edges of the bag 100 in the cephalad edge 128 half of the bag. The IV openings 302 are vertically aligned and parallel with the vertical edge of the bag 100. The IV openings 302 are used to facilitate access to the individual's arms when sealed within the bag. It is anticipated that these IV openings 302 will be approximately 4-16" in length. The IV openings 302 may be securely closed and sealed providing a waterproof seal when not opened.

It is preferred that zippers or metal of any kind would be avoided in conjunction with formation of the IV openings 302 as well as any other portion of the device 100. One reason for avoidance of metallic fittings is to avoid the risk of skin excoriation. Waterproof hook and loop closures or waterproof tongue and groove closures are the preferred means of closing and sealing the IV openings 302 because these reduce the risk of zipper failure which would be catastrophic. Further, these closures eliminate metal from the device in the event that an MM is ordered from the hospital while the patient is still submerged within the bag.

It should be apparent to one having ordinary skill in the relevant art, in light of the present disclosure, that a variety of other access or egress openings may be selectively formed and positioned about the sidewall 102 of the device 100. Such other openings may include an access port 304 that can include an attached or attachable retention bag 305 to provide a water resistant port that enables the insertion of a thermometer to monitor the water temperatures. Further other openings, envisioned and considered within the range of equivalents of the present invention but not specifically shown, may include:

A catheter opening. A catheter opening may be located along the center vertical axis of the top surface 124, so that it may be in line with an overheated individual's urinary tract in the event that a catheter needs to be implanted in the overheated individual while encapsulated in the device 100.

A rectal opening. A rectal opening may be located in along the center vertical axis of the bottom surface 126, so that it may be in line with an overheated individual's bowels in the event that a first responder needs to access the rectum for obtaining the overheated individual's core temperature through the use of a rectal thermometer or any other medical purpose while the overheated individual is encapsulated in the device 100.

Inlet and drainage portals 340. Inlet and drainage ports 340 are used to controllably introduce and drain the water 106 to and from the holding volume 104, as needed. The portals 340 are proximate to or made a part of the edges 128,130. The portals 340 forms apertures, preferably of a conventional size which would allow for medical personnel to connect an aftermarket conventional hospital hose to allows the medical personal to controllably add and drain the ice water 106/108 and dispose of the expelled ice water 106/108 in an appropriate manner.

Waterproof hook and loop closures or waterproof tongue and groove closures are the preferred means of closing and sealing any access or egress openings formed within the sidewall 124. These closures should eliminate metal from the device in the event that an Mill is ordered from the hospital while the patient is still submerged within the bag, while still retaining the ice water 106 within the internal holding volume 104 where the overheated individual is placed.

Figure 6:
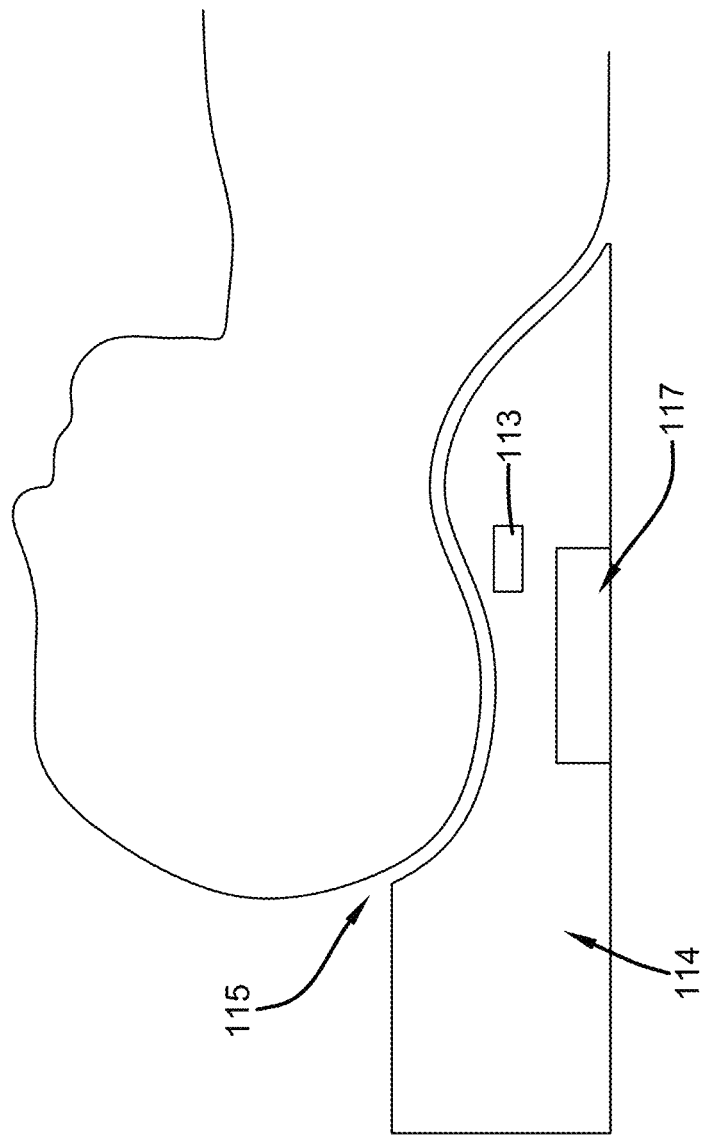
FIG. 6 is an elevation view of an individual's head on the waterproof pillow 114 with its occipital area nested in the pillow depression 115.

Referring now in conjunction with FIG. 6, a floating head support in the form of a waterproof pillow 114 is shown as provided in conjunction with the device 100. The waterproof pillow 114 is formed of a closed cell foam and, as such, is buoyant enough to raise the overheated individual's head above the waterline and out of the ice immersion bath and facilitates an open airway. The waterproof pillow 114 should be of a size that raises the overheated individuals head out of the water by about four inches. Further, the waterproof pillow contains a pillow depression 115. The pillow depression 115 is located in the center on the top surface of the waterproof pillow 114. The pillow depression 115 should be a round configuration with a depression depth of approximately two inches. The pillow depression 115 receives the occipital area of the overheated individual's head. When the occipital area of the overheated individual's head is placed in the pillow depression 115 the airway of the overheated individual is positioned in a manner that facilitates an open airway, so CPR may be performed with a greater likelihood of success, if necessary. The waterproof pillow 115 can be attached to the inside of ice immersion bag 100, through an waterproof pillow attachment means 117. It is anticipated that the waterproof pillow attachment means 117 will be a conventional hook and loop fastener.

Figure 7:
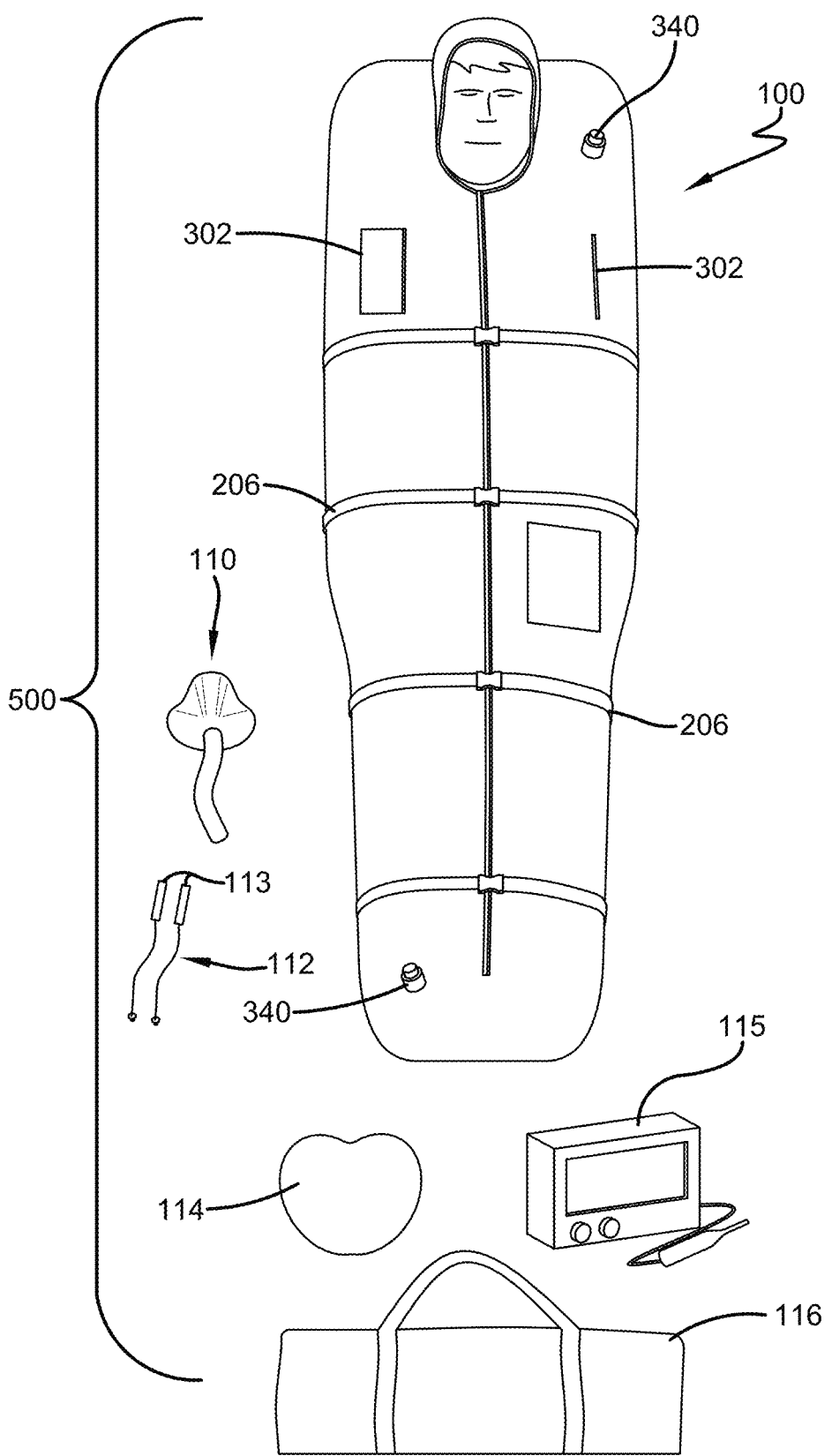
FIG. 7 is an illustrative view of an ice and water immersion therapy system utilizing an immersion device 100 as part of an overall kit 500.

Finally, referring now in conjunction with FIG. 7 it is envisioned that the bag 100 is provided as part of a kit 500 for the on-demand, reusable emergency application of ice water immersion therapy. The kit 500, anticipates comprising a plurality of any of the following items: a portable, reusable icewater immersion device or bag 100 as previously disclosed or described; a floating head support 114 a conventional cardiopulmonary resuscitation (CPR) mask 110, ear plugs 112, a waterproof pillow 114, a digital thermometer 115 for monitoring the temperature of the ice water 106/108, and a carrying case 116. Said ice immersion cooling bag 100 is the primary focus of the present invention. This kit effectively and aggressively provides cooling measures to an overheated individual through means ordinarily only available in a hospital or emergency room setting by a first responder, such as by an athletic trainer, an emergency medical technician or a paramedic.

Conventional ear plugs 112 are included with the emergency management system and are intended to be placed in the ear canal of the overheated individual. The ear plugs 112 may be placed into the ear canal before, during, or after the individual is placed within the ice immersion cooling bag 120. The ear plugs 112 are essential to the present invention because when an overheated person is submerged in the ice immersion cooling bag 100, the ear plugs prevent ice water 106/108 from entering the over heated individual's ear canal. The ear plugs 112 are an essential element of the present invention because if the ice water 106/108 enters the overheated individual's ear canal, the ice water can cause nystagmus of the eyes. However, nystagmus is ordinarily a sign of head trauma. Thus, if ice water 106/108 is in the ear canal and creating symptoms of nystagmus, there will be confusion by the treating physicians and nurses in the patient assessment. By implanting the ear plugs 112 in the ear canal, nystagmus may be reduced and prevent potential patient assessment confusions.

Further, nystagmus can cause vertigo which can lead to nausea and vomiting. It is anticipated that the ear plugs 112 will be made of a highly visible color such as yellow or orange. The ear plugs 112 can be attached to the 15 waterproof pillow 114, through an earplug attachment means 113. It is anticipated that the attachment means 113 will be a conventional hook and loop fastener.

The system 100 provides a carrying case 116. The carrying case 116 will be formed of conventional materials and used to transport the bag system 100 within the carrying case 116. It is anticipated that the functional limitations of the carrying case 116 will include all conventionally known types of transportation bags, within elements including but not limited to handles, straps, zippers, ties, buttons all made from conventionally known materials.

2. Operation of the Preferred Embodiment

In operation, the present invention can provide a useful means of effectively cooling an overheated individual. The overheated individual is placed within or is assisted and urged to enter the bag 100 through the entry portal 300. The individual's head is placed on the waterproof pillow 114 and their feed extended down toward the caudad edge 130.

The entry portal 300 is partially closed and sealed. While slightly open, ice water 106/108 is poured into the holding volume 104. The bag 100 is sealed and the cocooning straps 206 are utilized if necessary. The first responder continues to monitor the overheated individual until appropriate medical personnel relieve said first responder.

The foregoing descriptions of the specific embodiments are presented for purposes of illustration and description. They are not intended to be exhaustive nor to limit the invention to the precise forms disclosed and, obviously, many modifications and variations are possible in light of the above teaching. The embodiments are chosen and described in order to best explain principles of the invention and its practical application, and to thereby enable others skilled in the art to best utilize the invention and its various embodiments with various modifications as are suited to the particular use contemplated. It is intended that a scope of the invention be broadly defined by the Specification and Drawings appended hereto and to their equivalents; hence, the scope of the invention is to be limited only by the following claims.

What is claimed is:

1. A method for emergency application of ice water therapy comprising the steps of:
   a. obtaining a reusable device for the remote clinical emergency management of elevated body temperatures, said device forming a collapsible container for ice water immersion therapy, said collapsible container having an entry portal;

b. filling said collapsible container with ice water;
c. placing or guiding the entire body of an individual into said collapsible container via said entry portal in such a manner as to allow a face of said individual to remain exposed to prevent total immersion of said individual;
d. placing a head and neck of said individual upon a removable, buoyant, waterproof elevation pillow having an upper surface forming an occipital receiving recess to receive said head and maintain an open airway and prevent water from entering a nose or mouth of said individual; and
e. closing said entry portal and cocooning said collapsible container.

2. The method for emergency application of ice water therapy of claim 1, wherein said method is provided by a first responder, such as by an athletic trainer, an emergency medical technician or a paramedic.

3. The method for emergency application of ice water therapy of claim 2, wherein ear plugs are further provided and attached to said waterproof pillow via attachment means, said ear plugs being implanted into the individual's ear canal prior to ice water submersion to prevent medical illness due to water in the ear canal.

4. The method for emergency application of ice water therapy of claim 3, wherein said occipital receiving recess is round, and further comprises the step of placing the individual's head into said occipital receiving recess.

* * * * *